United States Patent [19]
Rubin et al.

[11] Patent Number: 5,827,662
[45] Date of Patent: Oct. 27, 1998

[54] METHODS FOR DETECTING GENETIC MUTATIONS RESULTING IN PROTEASE INHIBITOR INSUFFICIENCIES

[75] Inventors: Harvey Rubin, Philadelphia; Barry Cooperman, Penn Valley; Norman Schechter, Philadelphia; Michael Plotnick, Havertown; Zhi Mei Wang, Philadelphia, all of Pa.

[73] Assignee: The Trustees of the University of Pennsylvania, Philadelphia, Pa.

[21] Appl. No.: 722,268

[22] Filed: Dec. 18, 1996

Related U.S. Application Data

[63] Continuation-in-part of Ser. No. 276,936, Jul. 19, 1994, Pat. No. 5,612,194, which is a continuation-in-part of Ser. No. 229,286, Apr. 18, 1994, abandoned, which is a continuation-in-part of Ser. No. 221,171, Mar. 31, 1994, Pat. No. 5,723, 316, and Ser. No. 221,078, Mar. 31, 1994, Pat. No. 5,674, 708, each is a continuation-in-part of Ser. No.5,908, Jan. 15, 1993, Pat. No. 5,367,064, and a division of Ser. No. 735,335, Jul. 24, 1991, Pat. No. 5,252,725, which is a division of Ser. No. 370,704, Jun. 23, 1989, Pat. No. 5,079,336.

[51] Int. Cl.⁶ .............................. C12Q 1/00; C07K 14/81; C12N 15/15; C12N 15/70
[52] U.S. Cl. .......................... 435/6; 435/69.2; 435/172.3; 435/252.3; 435/252.33; 435/320.1; 435/7.71; 536/23.1; 536/23.5; 530/380
[58] Field of Search ................................ 435/69.2, 172.3, 435/252.3, 252.33, 320.1, 4, 6, 7.71, 7.72, 23; 530/380; 536/23.5

[56] References Cited

U.S. PATENT DOCUMENTS

| | | | |
|---|---|---|---|
| 5,079,336 | 1/1992 | Rubin et al. ............................. | 530/350 |
| 5,252,725 | 10/1993 | Rubin et al. ............................. | 536/23.5 |
| 5,266,465 | 11/1993 | Rubin et al. ............................. | 435/69.2 |
| 5,367,064 | 11/1994 | Rubin et al. ............................. | 536/23.2 |
| 5,612,194 | 3/1997 | Rubin et al. ............................. | 435/69.2 |
| 5,674,708 | 10/1997 | Cooperman et al. .................. | 435/69.2 |
| 5,723,316 | 3/1998 | Cooperman et al. .................. | 435/69.2 |

OTHER PUBLICATIONS

Eriksson, S., et al., Acta Medicia Scandinavica, vol. 220, "Familial alpha–1–antichymotrypsin deficiency", pp. 447–453, 1986.

Nakagawa, M., et al., Thrombosis Research, vol. 64, "Congenital antihrombin III deficiency (AT–III Kyoto): Identification of a point mutation altering arginine–406 to methionine behind the reactive site", pp. 101–108, 1991.

Sherman, P. M., et al., The Journal of Biological Chemistry, vol. 267, "Saturation mutagenesis of the plasminogen activator inhibitor–1 reactive center", pp. 7588–7595, 1992.

Poller, W., et al., Genomics, vol. 17, "A leucine–to–proline substitution causes a defective alpha1–antichymotrypsin allele associated with familial obstructive lung disease", pp. 740–743, 1993.

Cooperman, B. S. , et al., The Journal of Biological Chemistry, vol. 268, "Antichymotrypsin interaction with chymotrypsin", pp. 23616–23625, 1993.

Schechter, N. M., et al., The Journal of Biological Chemistry, vol. 268, "Reaction of human chymase with reactive site variants of alpha1–antichymotrypsin", pp. 23626–23633, 1993.

Jochmans, K., et al., Blood, vol. 83, "Antithrombin–Gly 424 Arg: A novel point mutation responsible for Type 1 anti-thrombin deficiency and neonatal thrombosis", pp. 146–151, 1994.

Carpenter et al., "A Transciptionally Amplified DNA Probe Assay with Ligatable Probes and Immunochemical Detection", 1993 Clin Chem., 39(9):1934–1938.

Eberwine et al., "Analysis of gene expression in single live neurons", 1992 Proc. Natl Acad. Sci., 89:30–10–30–14.

Joerger et al., "Analyte Detection with DNA–Labeled Antibodies and Polymerase Chain Reaction", 1995 Clin. Chem., 41(9):1371–1377.

Krieg and Melton, "Functional messenger RNAs are produced by SP6 in vitro transcription of cloned cDNAs", 1984 Nucl. Acid Res., 12:7057–7070.

Melton et al., "Efficient in vitro synthesis of biologically active RNA and RNA hybridization probes from plasmids containing a bacteriophage SP6 promoter", 1984 Nucl. Acid Res., 12:7035–7056.

Milligan et al., "Oligonucleotide synthesis using T7 RNA polymerase and synthetic DNA templates", 1987 Nucl. Acid Res., 15:8783–8798.

Mackler and Eberwine, "Diversity of Glutamate Receptor Subunit mRNA Expression within Live Hippocampal CA1 Neurons", 1993 Mol. Pharm., 44:308–315.

Ruzicka et al., "Immuno–PCR with a Commercially Available Avidin System", 1993 Science, 260:698–699.

Sanna et al., "Rapid induction of tumor necrosis factor α in the cerebrospinal fluid after intracerebroventricular injection of lipopolysaccharide revealed by a sensitive capture immuno–PCR assay ", 1995 Proc. Natl. Acad Sci., 92:272–275.

Sano et al., "Immuno–PCR: Very Sensitive Antigen Detection by Means of Specific Antibody–DNA Conjugates", 1992 Science, 258:120–122.

Sarkar and Sinner, "Access to a Messenger RNA Sequence of Its Protein Product Is Not Limited by a Tissue or Species Specificity", 1989 Science, 244:331–333.

Suzuki et al., "Double Determinant Immuno–Polymerase Chain Reaction: A Sensitive Method for Detecting Circulating Antigens in Human Sera", 1995 Jpn. J. Cancer Res., 86:885–889.

(List continued on next page.)

Primary Examiner—Robert A. Wax
Assistant Examiner—William W. Moore
Attorney, Agent, or Firm—Law Offices of Jane Massey Licata

[57] ABSTRACT

A method of producing a recombinant serine protease inhibitor capable of effectively modulating serine protease activity is provided. Compositions capable of modulating serine protease activity and use of such compositions to regulate inflammatory processes in cells are also provided.

6 Claims, No Drawings

OTHER PUBLICATIONS van Gelder et al., "Amplified RNA synthesized from limited quantities of heterogeneous cDNA", 1990 *Proc. Natl. Acad. Sci.*, 87:1663–1667

Zhou et al., Universal immuno–PCR for ultra–sensitive target protein detection:, 1993 *Nucleic Acid Res.*, 21:6038–6039.

Austin et al., "Site–directed mutagenesis of alanine–382 of human antithrombin III", FEBS Letter 280(2) :254–258, 1991.

Hopkins et al., "Effects of Mutations in the Hinge Region of Serpins", Biochemistry 32:7630–7657, 1993.

Davis et al, "C1 inhibitor hinge region mutations produce dysfunction by different mechanisms", Nature Genetics 1:354–358, 1992.

SEQUENCE LISTING ( 1 ) GENERAL INFORMATION:

( i i i ) NUMBER OF SEQUENCES: 34

( 2 ) INFORMATION FOR SEQ ID NO: 1:

( i ) SEQUENCE CHARACTERISTICS:
( A ) LENGTH: 4
( B ) TYPE: Amino Acid
( D ) TOPOLOGY: Linear ( x i ) SEQUENCE DESCRIPTION: SEQ ID NO: 1:

Ala Ala Pro Val
1

( 2 ) INFORMATION FOR SEQ ID NO: 2:

( i ) SEQUENCE CHARACTERISTICS:
( A ) LENGTH: 4
( B ) TYPE: Amino Acid
( D ) TOPOLOGY: Linear ( x i ) SEQUENCE DESCRIPTION: SEQ ID NO: 2:

Ala Ala Pro Phe
1

( 2 ) INFORMATION FOR SEQ ID NO: 3:

( i ) SEQUENCE CHARACTERISTICS:
( A ) LENGTH: 27
( B ) TYPE: Amino Acid
( D ) TOPOLOGY: Linear ( x i ) SEQUENCE DESCRIPTION: SEQ ID NO: 3:

Thr Glu Ala Ser Ala Ala Thr Ala Val Lys Ile Thr Leu Leu Ser
1               5                   10                  15
Ala Leu Val Glu Thr Arg Thr Ile Val Arg Phe Asn
                20                  25

( 2 ) INFORMATION FOR SEQ ID NO: 4:

( i ) SEQUENCE CHARACTERISTICS:
( A ) LENGTH: 27
( B ) TYPE: Amino Acid
( D ) TOPOLOGY: Linear ( x i ) SEQUENCE DESCRIPTION: SEQ ID NO: 4:

Thr Glu Ala Ser Ala Ala Thr Ala Val Lys Ile Thr Leu Met Ser
1               5                   10                  15
Ala Leu Val Glu Thr Arg Thr Ile Val Arg Phe Asn
                20                  25

( 2 ) INFORMATION FOR SEQ ID NO: 5:

( i ) SEQUENCE CHARACTERISTICS:
( A ) LENGTH: 27
( B ) TYPE: Amino Acid
( D ) TOPOLOGY: Linear ( x i ) SEQUENCE DESCRIPTION: SEQ ID NO: 5:

Thr Glu Ala Ser Ala Ala Thr Ala Val Lys Ile Thr Leu Arg Ser
1               5                   10                  15
Ala Leu Val Glu Thr Arg Thr Ile Val Arg Phe Asn
                20                  25

( 2 ) INFORMATION FOR SEQ ID NO: 6:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 6:

```
Thr Glu Ala Ser Ala Ala Thr Ala Val Lys Ile Thr Leu Trp Ser
1               5                   10                  15
Ala Leu Val Glu Thr Arg Thr Ile Val Arg Phe Asn
                20                  25
```

( 2 ) INFORMATION FOR SEQ ID NO: 7:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 7:

```
Thr Glu Ala Ser Ala Ala Thr Ala Val Lys Ile Thr Leu Leu Ser
1               5                   10                  15
Ala Val Val Glu Thr Arg Thr Ile Val Arg Phe Asn
                20                  25
```

( 2 ) INFORMATION FOR SEQ ID NO: 8:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 8:

```
Thr Glu Ala Ser Ala Ala Thr Ala Val Lys Ile Ile Pro Met Ser
1               5                   10                  15
Ile Pro Val Glu Thr Arg Thr Ile Val Arg Phe Asn
                20                  25
```

( 2 ) INFORMATION FOR SEQ ID NO: 9:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 9:

```
Thr Glu Ala Ser Ala Ala Thr Ala Leu Glu Ala Ile Pro Met Ser
1               5                   10                  15
Ile Pro Val Glu Thr Arg Thr Ile Val Arg Phe Asn
                20                  25
```

( 2 ) INFORMATION FOR SEQ ID NO: 10:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 10:

```
Thr Glu Ala Ser Gly Thr Thr Ala Val Lys Ile Thr Leu Leu Ser
1               5                   10                  15
Ala Leu Val Glu Thr Arg Thr Ile Thr Arg Phe Asn
                20                  25
```

( 2 ) INFORMATION FOR SEQ ID NO: 11:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 11:

```
Thr Glu Ala Ser Gly Thr Thr Ala Val Lys Ile Thr Leu Phe Ser
1               5                   10                  15
Ala Leu Val Glu Thr Arg Thr Ile Thr Arg Phe Asn
                20                  25
```

( 2 ) INFORMATION FOR SEQ ID NO: 12:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 12:

```
Thr Glu Ala Ser Gly Thr Thr Ala Val Lys Ile Thr Leu Met Ser
1               5                   10                  15
Ala Leu Val Glu Thr Arg Thr Ile Thr Arg Phe Asn
                20                  25
```

( 2 ) INFORMATION FOR SEQ ID NO: 13:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 13:

```
Thr Glu Ala Ser Gly Thr Thr Ala Val Lys Ile Ile Pro Met Ser
1               5                   10                  15
Ile Pro Val Glu Thr Arg Thr Ile Thr Arg Phe Asn
                20                  25
```

( 2 ) INFORMATION FOR SEQ ID NO: 14:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 14:

```
Thr Glu Ala Ser Gly Thr Thr Ala Val Lys Ile Ile Pro Leu Ser
1               5                   10                  15
Ile Pro Val Glu Thr Arg Thr Ile Thr Arg Phe Asn
                20                  25
```

( 2 ) INFORMATION FOR SEQ ID NO: 15:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 15:

```
Thr Glu Ala Ser Gly Thr Thr Ala Val Lys Val Ile Ser Ala Glu
1               5                   10                  15
Trp Met Val Glu Thr Arg Thr Ile Thr Arg Phe Asn
                20                  25
```

(2) INFORMATION FOR SEQ ID NO: 16:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 16:

```
Thr Glu Ala Ser Gly Thr Met Phe Leu Glu Ala Ile Pro Met Ser
1               5                   10                  15
Ile Pro Pro Glu Thr Arg Thr Ile Thr Arg Phe Asn
                20                  25
```

(2) INFORMATION FOR SEQ ID NO: 17:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 17:

```
Thr Glu Ala Ser Gly Thr Met Phe Leu Glu Ala Ile Pro Met Ser
1               5                   10                  15
Ile Pro Pro Glu Thr Arg Thr Ile Ala Arg Phe Asn
                20                  25
```

(2) INFORMATION FOR SEQ ID NO: 18:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 18:

```
Thr Glu Ala Ser Gly Thr Met Phe Leu Glu Ala Ile Pro Met Ser
1               5                   10                  15
Ile Pro Pro Glu Val Lys Phe Asn Thr Arg Phe Asn
                20                  25
```

(2) INFORMATION FOR SEQ ID NO: 19:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 19:

```
Arg Glu Ala Ser Ala Ala Thr Ala Val Lys Ile Thr Leu Leu Ser
1               5                   10                  15
Ala Leu Val Glu Thr Arg Thr Ile Val Arg Phe Asn
                20                  25
```

(2) INFORMATION FOR SEQ ID NO: 20:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 20:

```
Thr Glu Arg Ser Ala Ala Thr Ala Val Lys Ile Thr Leu Leu Ser
1               5                   10                  15
Ala Leu Val Glu Thr Arg Thr Ile Val Arg Phe Asn
                20                  25
```

( 2 ) INFORMATION FOR SEQ ID NO: 21:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 21:

```
Thr Glu Ala Ser Ala Arg Thr Ala Val Lys Ile Thr Leu Leu Ser
1               5                   10                  15
Ala Leu Val Glu Thr Arg Thr Ile Val Arg Phe Asn
                20                  25
```

( 2 ) INFORMATION FOR SEQ ID NO: 22:

( i ) SEQUENCE CHARACTERISTICS:
        ( A ) LENGTH: 23
        ( B ) TYPE: Amino Acid
        ( D ) TOPOLOGY: Linear ( x i ) SEQUENCE DESCRIPTION: SEQ ID NO: 22:

```
Thr Glu Ala Ser Gly Thr Thr Ala Val Lys Ile Ile Pro Met Ser
1               5                   10                  15
Ile Pro Pro Glu Thr Arg Phe Asn
                20
```

( 2 ) INFORMATION FOR SEQ ID NO: 23:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 23:

```
Thr Glu Ala Ser Ala Ala Thr Ala Val Lys Ile Ile Pro Arg Ser
1               5                   10                  15
Ile Pro Val Glu Thr Arg Thr Ile Val Arg Phe Asn
                20                  25
```

( 2 ) INFORMATION FOR SEQ ID NO: 24:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 24:

```
Thr Glu Ala Ser Ala Ala Thr Ala Val Lys Ile Met Pro Leu Ser
1               5                   10                  15
Thr Gln Val Glu Thr Arg Thr Ile Val Arg Phe Asn
                20                  25
```

( 2 ) INFORMATION FOR SEQ ID NO: 25:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 25:

```
Thr Glu Ala Ser Ala Ala Thr Ala Val Lys Ile Ala Gly Arg Ser
1               5                   10                  15
Leu Asn Val Glu Thr Arg Thr Ile Val Arg Phe Asn
                20                  25
```

( 2 ) INFORMATION FOR SEQ ID NO: 26:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 26:

```
Thr Glu Ala Ser Ala Ala Thr Ala Val Lys Ile Val Ala Arg Thr
1               5                   10                  15
Leu Leu Val Glu Thr Arg Thr Ile Val Arg Phe Asn
                20                  25
```

( 2 ) INFORMATION FOR SEQ ID NO: 27:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 27:

```
Thr Glu Ala Ser Ala Ala Thr Ala Val Lys Ile Ser Ala Arg Met
1               5                   10                  15
Ala Pro Val Glu Thr Arg Thr Ile Val Arg Phe Asn
                20                  25
```

( 2 ) INFORMATION FOR SEQ ID NO: 28:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 28:

```
Thr Glu Ala Ser Ala Ala Thr Ala Val Lys Ile Met Ser Arg Met
1               5                   10                  15
Ser Leu Val Glu Thr Arg Thr Ile Val Arg Phe Asn
                20                  25
```

( 2 ) INFORMATION FOR SEQ ID NO: 29:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 29:

```
Thr Glu Ala Ser Ala Ala Thr Ala Val Lys Ile Thr Phe Arg Ser
1               5                   10                  15
Ala Arg Val Glu Thr Arg Thr Ile Val Arg Phe Asn
                20                  25
```

( 2 ) INFORMATION FOR SEQ ID NO: 30:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 30:

```
Thr Glu Ala Ala Gly Ala Met Phe Leu Glu Ala Ile Pro Met Ser
1               5                   10                  15
Ile Pro Pro Glu Val Lys Phe Asn Lys Pro Phe Thr
                20                  25
```

(2) INFORMATION FOR SEQ ID NO: 31:

(i) SEQUENCE CHARACTERISTICS:
        (A) LENGTH: 20
        (B) TYPE: Amino Acid
        (D) TOPOLOGY: Linear (xi) SEQUENCE DESCRIPTION: SEQ ID NO: 31:

```
Ala Ala Thr Ala Val Lys Ile Thr Leu Leu Ser Ala Leu Val Glu
1               5                   10                  15
Thr Arg Thr Ile Val
                20
```

(2) INFORMATION FOR SEQ ID NO: 32:

(i) SEQUENCE CHARACTERISTICS:
        (A) LENGTH: 20
        (B) TYPE: Amino Acid
        (D) TOPOLOGY: Linear (xi) SEQUENCE DESCRIPTION: SEQ ID NO: 32:

```
Gly Thr Met Phe Leu Glu Ala Ile Pro Met Ser Ile Pro Pro Glu
1               5                   10                  15
Val Lys Phe Asn Thr
                20
```

(2) INFORMATION FOR SEQ ID NO: 33:

(i) SEQUENCE CHARACTERISTICS:
        (A) LENGTH: 15
        (B) TYPE: Amino Acid
        (D) TOPOLOGY: Linear (xi) SEQUENCE DESCRIPTION: SEQ ID NO: 33:

```
Ala Ala Thr Ala Val Lys Ile Thr Leu Leu Ser Ala Leu Val Glu
1               5                   10                  15
```

(2) INFORMATION FOR SEQ ID NO: 34:

(i) SEQUENCE CHARACTERISTICS:
        (A) LENGTH: 15
        (B) TYPE: Amino Acid
        (D) TOPOLOGY: Linear (xi) SEQUENCE DESCRIPTION: SEQ ID NO: 34:

```
Gly Thr Met Phe Leu Glu Ala Ile Pro Met Ser Ile Pro Pro Glu
1               5                   10                  15
```

METHODS FOR DETECTING GENETIC MUTATIONS RESULTING IN PROTEASE INHIBITOR INSUFFICIENCIES

This application is a continuation-in-part application of U.S. application Ser. No. 08/276,936, filed Jul. 19, 1994, now U.S. Pat. No. 5,612,194, which is a continuation-in-part application of U.S. application Ser. No. 08/229,286, filed Apr. 18, 1994, now abandoned, which is a continuation-in-part of U.S. application Ser. No. 08/221,078, filed Mar. 31, 1994, now U.S. Pat. No. 5,674,708, and U.S. application Ser. No. 08/221,171, filed Mar. 31, 1994, now U.S. Pat. No. 5,723,316, each of which is a continuation-in-part of application Ser. No. 08/005,908, filed Jan. 15, 1993, now U.S. Pat. No. 5,367,064, both of which are divisionals of Application Ser. No. 07/735,335, filed Jul. 24, 1991, now U.S. Pat. No. 5,252,725, which is a divisional of application Ser. No. 07/370,704, filed Jun. 23, 1989, now U.S. Pat. No. 5,079,336.

BACKGROUND OF THE INVENTION

Serine protease inhibitors or "serpins" are a superfamily of inhibitors involved in the mediation of a variety of biological processes essential to survival of a host. Members of the serpin family play a role in a great number of biological processes including, but not limited to, inflammation, fertilization, tumor migration, neurotropism, and heat shock. Maspin was recently identified and characterized as a protective serpin normally present in mammary epithelium but absent from most mammary carcinoma cell lines. Serpins are found in plants, prokaryotes, insects and animals. Natural mutations and modifications of serpins are correlated with a number of serious disease states. Serpin dysfunction is associated with lung, liver and blood coagulation diseases such as emphysema, liver cirrhosis, thrombosis and pulmonary embolism.

The interaction of serpins with endogenous and microbial proteases produces a spectrum of molecular species, each of which are components of a highly evolutionarily conserved homeostatic mechanism that operates to maintain concentrations of intact, active serpins essential to a host's survival. For example, the serpin-protease complex and the hydrolyzed, inactive form of the intact serpin stimulate the production of interleukin-6, signaling hepatocytes to increase synthesis of the acute phase proteins including a subpopulation of the serpin superfamily of proteins. While serpin-enzyme complexes are rapidly cleared from the circulation, cleaved and intact forms of these complexes can accumulate in local areas of inflammation. This accumulation establishes a complex microenvironment of chemoattractants and inhibitors of chemotaxis as well as activators and inhibitors of neutrophil degranulation, leukotrienes, platelet activating factor (PAF), and superoxide production. The extreme virulence of several pox viruses has been attributed in part to a serpin whose target is cysteine proteinase ICE, the interleukin 1-β converting enzyme.

Through various animal models, it has been demonstrated that uncontrolled serine protease activity is a major mechanism of lung injury and that an appropriate serpin response controls the degree of the injury. For example, antithrombin III (ATIII) in combination with α-1-protease inhibitor (α1P1), protected sheep from endotoxin-induced lung injury where the individual serpins were not as effective as the combination. Redens et al., *Circ. Shock* 1988, 26, 15. Redens et al. also showed that ATIII protects against the development of disseminated intravascular coagulation in endotoxemic rats. Emerson et al., *Circ. Shock* 1987, 21, 1. A scavenger of $H_2O_2$ and a chloromethyl ketone inhibitor of elastase blocked reactive oxygen potentiation of neutrophil elastase-mediated acute edematous lung injury in a rat and α1P1 diminished bleomycin-mediated pulmonary inflammation as well as subsequent fibrosis. Baird et al., *Physiol.* 1986, 61, 2224 and Nagai et al., *Am. Rev. Resp. Dis.* 1992, 145, 651. In another system, however, neutrophil elastase inhibitors, Eglin C and a low molecular weight compound L 658,758, failed to inhibit leukotriene B4-induced-neutrophil-mediated adherence, diapedesis or vascular leakage. Rosengren et al., *Am J. Physiol.* 1990, 259, H1288. As shown by these studies, inhibitors of proteolytic enzymes administered therapeutically can limit the molecular and cellular mechanism of inflammation and reduce tissue damage.

There are two subfamilies within the serpin superfamily. One family contains proteins for which no cognate serine proteases have yet been identified. Examples of proteins in this subfamily include ovalbumin, angiotensinogen and steroid binding globulins. The second family contains members for which at least one serine protease can be found as an inhibitory target. The subfamily of serpins that inhibit serine proteases have characteristic properties that define the activity of the inhibitor, i.e., second order rate constants for inhibition of their cognate enzyme range between $10^2$ and $10^7$ $M^{-1}s^{-1}$; the enzyme-inhibitor complex is stable under certain conditions and can be detected as a species with a molecular weight greater than the individual components in SDS polyacrylamide gels; and, a large conformational change occurs upon cleavage of the sessile bond in the reactive center leading to increased thermal stability of the protein. An example of a serpin in this subfamily is α1-antichymotrypsin (ACT), an inhibitor of chymotrypsin (Chtr). ACT is synthesized predominantly by the liver and is one of the acute phase reactants with levels rising rapidly to more than 5 fold in response to a wide variety of injuries including surgery, acute myocardial infarctions, burns, autoimmune diseases, malignancies, infections and liver allograft rejection. ACT has also been linked with the plasticity of the nervous system and associated with beta amyloid deposits in Alzheimer's disease, in aging brain, Down's syndrome and in the Dutch variant of hereditary cerebral hemorrhage with amyloidosis. It has been demonstrated that both native ACT and recombinant ACT (rACT) inhibit superoxide generation by human neutrophils in suspension.

In general, the reactive loop of an inhibitory serpin is comprised of a relatively short amino acid sequence. The selectivity of serpins for inhibiting a specific type of protease depends on the amino acid sequence of a reactive center region exposed on the surface of the serpin. Jiang H. et al., *J. Biol. Chem.* 1994, 269, 55–58, demonstrated that the selectivity of serpins from a lepidopteran insect, *Manduca sexta,* can be altered by changing the amino acid sequence in the reactive loop. It was found that pre-mRNA splicing generates inhibitor diversity and the potential to regulate a variety of proteinases, using the same protein framework joined to different reactive site region cassettes.

Based upon three dimensional structures of complexes formed by small inhibitors (about 50 amino acids) with their target enzymes, it is believed that the P3–P3' region, amino acids 356–361 in ACT, (nomenclature of Schecter I. and Berger A. C. *Biochemistry Biophysics Research Communication* 1967, 27:157), in the loop of serpins, or so-called "active site region" (or bait region) serves as a primary contact site or binding site with the protease. It has now been found that another part of the loop (from P14 to P9), denoted the "hinge region", is also important for the inhibitory activities of serpins. A method has now been developed for modulating serine protease activity in cells or tissues which comprises selecting a target protease which accumulates in cells or tissues, producing a recombinant serine protease inhibitor having a protease binding site and a hinge region of a reactive center loop which have modified amino acid sequences so that interaction between the inhibitor and the target protease is altered, and contacting cells or tissues with the modified serine protease inhibitor so that serine protease activity is modulated. Compositions capable of effectively modulating serine protease activity which comprise a recombinant serine protease inhibitor having a protease binding site and a hinge region of a reactive loop which have modified amino acid sequences are also provided. These compositions are useful in regulating inflammatory processes. In addition, a method is provided for producing serine protease inhibitors capable of effectively modulating the activity of the serine proteases which comprises determining a sequence of a serine protease inhibitor; identifying a reactive loop of said serine protease inhibitor, said reactive loop containing a first amino acid sequence of a protease binding site and a second amino acid sequence of a hinge region; modifying the first amino acid sequence of said protease binding site so that the selectivity of a recombinant serine protease inhibitor for other proteases is altered; modifying the second amino acid sequence of said hinge region so that said recombinant serine protease inhibitor is capable of effectively modulating the activity of the serine protease; and synthesizing this modified serine protease inhibitor.

SUMMARY OF THE INVENTION

An object of the present invention is to provide a method of producing a recombinant serine protease inhibitor capable of effectively modulating serine protease activity which comprises determining a sequence of a selected serine protease inhibitor; identifying a reactive loop of said serine protease inhibitor, said reactive loop containing a first amino acid sequence of a protease binding site and a second amino acid sequence of a hinge region; modifying the first amino acid sequence of said protease binding site so that the selectivity of a recombinant serine protease inhibitor for other proteases will be altered; modifying the second amino acid sequence of said hinge region so that said recombinant serine protease inhibitor will effectively modulate an activity of the protease; and synthesizing the modified recombinant serine protease inhibitor.

Another object of the present invention is to provide a composition capable of effectively modulating serine protease activity which comprises a recombinant serine protease inhibitor having a protease binding site and a hinge region of a reactive loop which have modified amino acid sequences.

Yet another object of the present invention is to provide a method of modulating a serine protease activity in cells or tissues which comprises selecting a target protease which accumulates in cells or tissues; producing a recombinant serine protease inhibitor having a protease binding site and a hinge region of a reactive center loop which have modified amino acid sequences so that interaction between the inhibitor and the target protease is altered; and contacting cells or tissues with the modified serine protease inhibitor so that serine protease activity is modulated.

Yet another object of the present invention is to provide analogues of human α-1-antichymotrypsin which are efficient inhibitors of chymotrypsin.

Also provided are nucleic acid sequences encoding serine protease inhibitors including the α-1-antichymotrypsin analogues, expression vectors comprising these nucleic acid sequences, transformed host cells capable of expressing these nucleic acid sequences, cell cultures capable of expressing serine protease inhibitors and protein preparations comprising these serine protease inhibitors.

DETAILED DESCRIPTION OF THE INVENTION

Serine protease inhibitors of the serpin superfamily of glycoproteins are important in maintaining homeostasis in the body. Serpins regulate proteases involved in a range of important biological processes including, but not limited to, blood coagulation, fertilization and inflammation. The various serpins in animals and insects are believed to have evolved through gene duplication and divergence, resulting in a large number of serpin genes within a single organism, each encoding a protein with a unique reactive site region and physiological function. An example of a serpin is antichymotrypsin (ACT) which inhibits chymotrypsin, pancreatic elastase, mast cell chymase and cathepsin G. Elevated levels of ACT have been observed in a wide variety of injuries including surgery, acute myocardial infarctions, burns, autoimmune diseases, malignancies, infections and liver allograft rejection.

ACT has been associated with certain cell mediated and cytokine mediated events. For example, tumor necrosis factor enhances platelet activation through TNF-mediated release of cathepsin G from neutrophils. This effect can be blocked by ACT. In addition, the synthesis and release of leukotriene B4 and platelet activating factor from TNF-stimulated neutrophils can be blocked by ACT. Neutrophil cathepsin G and mast cell chymase are major components in the inflammatory response in skin and in the lung. Therefore, it has been suggested that ACT plays a regulatory role in limiting inflammation that arises secondary to the release of the enzymatic contents of the granules. Native and recombinant ACT have also been shown to inhibit superoxide generation by human neutrophils. In the intact cell system, both intact ACT and ACT complexed with chymotrypsin were found equally effective in inhibiting free radical production by human neutrophils stimulated with either f-Met-Leu-Phe, Con A or PMA. Families with only 50% of normal circulating ACT have been found to have abnormalities in lung function with large residual volumes and an increase in atopic diseases. Thus, it appears that intact ACT, as well as cleaved and complexed forms of ACT, play a central role in regulating inflammation and certain developmental events.

ACT shares a number of properties with other members in the serpin family. The most important feature of ACT and other serpins which retain inhibitory activity and specificity is the presence of a mobile reactive loop.

Serine protease inhibitors or "serpins" are believed to inhibit their target serine proteases in accordance with the following general mechanism. The serines protease requires the serpin as a substrate, and initiates proteolytic attack. Serpins form tight 1:1 complexes with their target proteases through an interaction with a specific site, the P1 residue. The standard notation denotes the P1 position as the position immediately N terminal to the cleavage site, P2 is N terminal to P1, and so forth. The P1 position is located in an exposed region of the serpin referred to as the reactive loop. There is a large body of structural data derived from peptide inhibitors demonstrating that the reactive loop of the inhibitor is in an antiparallel beta strand conformation, referred to as "canonical". However, it has now been found that the reactive loop of an intact serpin assumes a somewhat distorted helical conformation with the P1 side chain extending outwardly from the rest of the serpin. The reactive loop is not preorganized in a canonical, antiparallel beta strand conformation, but rather there appears to be subsequent helix destabilization for productive binding with the protease. Binding to the protease induces a conformational change in the serpin, which under certain conditions, propagates to alter the conformation of the protease itself. The altered conformation of the protease effectively eliminates its enzymatic activity, and thus the enzymatic reaction pathway of the protease is arrested.

An important focus of serpin research has been the relationship between an imbalance between serpins and their target enzymes and tissue destruction and degenerative diseases. Through a detailed investigation of the biochemical and structural properties of the interaction of serpins, and genetically engineered variants of serpins, with target proteases, a rational design of new proteins having therapeutic activity has now been developed. According to a 3-dimensional model of complexes formed by small peptide inhibitors (about 50 amino acids) with their target enzymes, it is believed that the P3–P3' region in the loop of serpins, also referred to as the "active site region" or the "bait region" serves as the primary contact site or binding site with the enzyme. The inhibitory activity of a serpin for a selected enzyme can be altered by modifying amino acids, either by mutation or deletion, in this protease binding site region. For example, it was found that substituting a leucine with a methionine at the P1' position of wild type ACT resulted in a mutant with the ability to partially inhibit human neutrophil elastase, while maintaining its ability to inhibit chymotrypsin, cathepsin-G and chymase (See Tables 1 and 2). It was also found that a variant in which the P6'–P9' residues of the reactive loop were deleted retained serine protease inhibitory activity against chymotrypsin and enhanced the activity against human neutrophil elastase. The activities of human neutrophil elastase, chymotrypsin, cathepsin G and chymase were measured in accordance with methods described in Examples 2 through 5 of this application. Plasmin and thrombin activities were also measured in accordance with methods well known in the art, for example Cooperman et al., *J. Biol. Chem.* 1993, 268, 23616.

It has also been found that the hinge region (P14–P9) is an important component of the loop for maintaining the inhibitory activity of serpins. Amino acid sequence alignment has shown that the hinge region of each inhibitory serpin is strongly conserved for amino acids with small and neutral side chains, such as alanines or threonines, as opposed to charged residues such as arginine and glutamic acid. The replacement of threonine at P14 with arginine in a recombinant ACT (rACT) leads to a substrate which has lost its inhibitory activity (See Tables 1 and 2).

In the present invention, a method is provided for producing a recombinant serine protease inhibitor capable of effectively modulating their activities. In this method, a sequence of a selected serine protease inhibitor is determined and the reactive loop of the serine protease inhibitor is identified. The amino acid sequence of the protease binding site of this loop is then modified to alter the selectivity of the serine protease inhibitor for various other proteases. Modifications to the protease binding site can comprise substitution or deletion of one or more amino acids in the sequence. In a preferred embodiment, the modification will consist of substituting a few amino acids in the protease binding site region with amino acids known to be in other serine protease inhibitors. For example, the substitution of the leucine at the P1' position of ACT with a methionine (which is the amino acid present at this position in the serpin α1P1, an inhibitor of human neutrophil elastase) results in a mutant with the ability to inhibit chymotrypsin, cathepsin-G, chymase and human neutrophil elastase (see Tables 1 and 2). Appropriate substitutions in the amino acid sequence of the protease binding site can be routinely determined by one of skill in the art in accordance with the teachings of the present invention. The amino acid sequence of the hinge region can also be modified. In a preferred embodiment, the hinge region is modified to contain primarily amino acids having small, neutral chains, such as alanines or threonines. This modified recombinant serine protease inhibitor is then synthesized. Modifications can be performed using standard site-directed mutagenesis techniques well known to those of skill in the art.

In one embodiment of the present invention, the method is used to produce analogues of ACT. ACT appears to be unique among serpins in its ability to bind DNA. ACT has been localized in the nuclei of certain malignant and non-malignant cells and has been reported to inhibit DNA polymerase alpha, DNA synthesis in permeabilized human carcinoma cells, and poly-C-dependent primase, and to stimulate poly dT dependent primase. It has now been found that lysine residues within two short regions of rACT are important for DNA binding. rACT has two elements, a stretch of lysines (residues 210–212) and the C terminal peptide 390–398, containing two lysines which are involved in DNA binding interaction. Replacement of the lysines 210–212 by glutamates or threonines resulted in the complete loss of DNA binding activity. Partial DNA binding activity was retained upon replacement of only one or two of the lysines with threonine. With respect to the C-terminal peptide, it was found that acetylation of K396, the most reactive lysine in rACT, was diminished in the presence of DNA, and replacement of the two lysines, K391 and K396, with threonine resulted in a protein with very little DNA binding capability. Therefore, when producing and selecting recombinant ACT analogues, further modifications can be made at lysines 210–212 and in the C terminal peptide, 390–398 so that DNA binding of the inhibitor is modulated.

Studies on the interactions between serpins and serine proteases have shown that the conformational change accompanying binding of the serpin to the protease is important in the inhibition of a selected serine protease activity.

In accordance with the teachings of the present invention compositions are also provided which are capable of effectively modulating serine protease activity. A composition of the present invention comprises a recombinant serine protease inhibitor having a protease binding site and a hinge region of a reactive loop which have modified amino acid sequences. In a preferred embodiment the modified amino acid sequence of the hinge region comprises amino acids with small and neutral side chains such as alanines and threonines. Compositions of the present invention are especially useful in regulating inflammatory processes related to serine proteases accumulating in cells or tissues.

A method of modulating a serine protease activity in cells or tissues is also provided in the present invention. This method comprises selecting a target protease which accumulates in cells or tissues, producing a recombinant serine protease inhibitor having a protease binding site and a hinge region of a reactive center loop which have modified amino acid sequences so that interaction between the inhibitor and the target protease is altered and contacting cells or tissues with the modified serine protease inhibitor so that activity of the serine protease is modulated. It is preferred that the amino acid sequence of the hinge region of the serine protease inhibitor be modified with amino acids having small and neutral side chains such as alanines and threonines.

In one embodiment the serine protease activity modulated is chymase activity. In this embodiment it is preferred that the serine protease inhibitor be an analogue of human wild type α-1-antichymotrypsin having a modification of amino acid 358 or a modification of amino acids 356–361.

In another embodiment, the serine protease activity modulated is elastase activity. In this embodiment it is preferred that the serine protease inhibitor be an analogue of human wild type α-1-antichymotrypsin having a modification of amino acid 358 or a modification of amino acids 356–361.

In particular, the present invention provides recombinantly produced serine protease inhibitors which are α-1-antichymotrypsin analogues. These analogues are efficient inhibitors of chymotrypsin. For example, an analogue of α-1-antichymotrypsin is provided by the present invention, wherein the amino acid corresponding to alanine at amino acid position 350 of wild type α-1-antichymotrypsin is substituted with arginine. An analogue of human wild type α-1-antichymotrypsin wherein the amino acids corresponding to Ala-Ala-Thr-Ala-Val-Lys-Ile-Thr-Leu-Leu-Ser-Ala-Leu-Val-Glu-Thr-Arg-Thr-Ile-Val (SEQ ID NO: 31) at amino acid positions 349 to 368 of wild type α-1-antichymotrypsin are substituted with Gly-Thr-Met-Phe-Leu-Glu-Ala-Ile-Pro-Met-Ser-Ile-Pro-Pro-Glu-Val-Lys-Phe-Asn-Thr (SEQ ID NO: 32) is also provided. This analogue is -referred to as rACT-P10P10'. In addition, a human wild type α-1-antichymotrypsin analogue is provided wherein the amino acids corresponding to Ala-Ala-Thr-Ala-Val-Lys-Ile-Thr-Leu-Leu-Ser-Ala-Leu-Val-Glu (SEQ ID NO: 33) at amino acid positions 349 to 363 of wild-type α-1-antichymotrypsin are substituted with Gly-Thr-Met-Phe-Leu-Glu-Ala-Ile-Pro-Met-Ser-Ile-Pro-Pro-Glu (SEQ ID NO: 34), and the amino acid Val at position 368 is substituted with Ala. This analogue is referred to as rACT-P10P5'. The analogues of the present invention can be produced from nucleotide sequences corresponding to the amino acid substitutions identified herein. Proteins having an amino acid sequence containing more or fewer amino acids, fragments, or differing by one or more amino acids from the sequences of the α-1-antichymotrypsin analogues disclosed herein that have antichymotrypsin, anti-trypsin, anti-thrombin, and antihuman neutrophil elastase (HNE) activity are also within the scope of the present invention.

The present invention also provides nucleic acid sequences encoding recombinant serine protease inhibitors including these α-1-antichymotrypsin analogues, expression vectors comprising these nucleic acid sequences, transformed host cells capable of expressing these nucleic acid sequences, cell cultures capable of expressing recombinant serine protease inhibitors such as the analogues of human α-1-antichymotrypsin of the present invention and protein preparations comprising recombinant serine protease inhibitors such as the analogues of human α-1-antichymotrypsin.

Generally, recombinant serine protease inhibitors including the α-1-antichymotrypsin analogues are produced in host cells that are transformed with an expression vector comprising a nucleic acid sequence coding for the particular recombinant serine protease inhibitor. The host cells are cultured under conditions whereby the nucleic acid sequence coding for the particular serine protease inhibitor is expressed. After a suitable amount of time for the product to accumulate, the inhibitor is purified from the host cells or medium surrounding the cells.

Host cells and expression vectors suitable for use in the invention may be routinely selected to form an expression system capable of producing a recombinant serine protease inhibitor such as the α-1-antichymotrypsin analogues. Host cells suitable for use in the present invention include prokaryotic and eukaryotic cells that can be transformed to stably contain and express these recombinant serine protease inhibitors. Suitable cells include bacterial, yeast, and mammalian cells. When prokaryotic host cells are used, no glycosylation of the serine protease inhibitor will occur. However, surprisingly it has been found that the unglycosylated serine protease inhibitor, human α-1-antichymotrypsin, displays substantial functional similarity with native human serum α-1-antichymotrypsin and, thus, the unglycosylated, recombinant serine protease inhibitors are expected to be effective substitutes for the native serine protease inhibitors in therapeutic applications. The bacterium E. coli is preferred for the production of the protein products as cloning and expression can be rapidly obtained. In addition, production of E. coli is readily amenable to cost-effective, large-scale fermentation and protein purification. Introduction of an expression vector incorporating a nucleic acid sequence encoding for a recombinant serine protease inhibitor into a host cell can be performed in a variety of ways such as calcium chloride or lithium chloride treatment or electroporation.

The expression vector comprising a nucleic acid sequence coding for a recombinant serine protease inhibitor such as a human α-1-antichymotrypsin analogue preferably further comprises transcription and translation control elements operatively linked to the nucleic acid sequence coding the recombinant serine protease inhibitor; for example, in an upstream position, a promoter, followed by a translation initiation signal comprising a ribosome binding site, and an initiation codon, and, in a downstream position a transcription termination signal. The transcription and translation control elements may be ligated in any functional combination or order. The transcription and translation control elements used in any particular embodiment of the invention will be chosen with reference to the type of cell into which the expression vector will be introduced so that an expression system is created.

It is preferable to use a strong promoter, such as E. coli trp-lac promoter or the T7 $P_L$ promoter, to ensure high levels of expression of the protein product. The p1Nomp and β-lactamase promoters have been found to give low or no yields of β-1-antichymotrypsin when operatively linked with DNA coding for α-1-antichymotrypsin. It is also preferable that the promoter be an inducible promoter, such as the $P_L$ promoter, to avoid possible host toxicity during accumulation of the product.

Alternatively, a gene expression system based on bacteriophage T7 RNA polymerase as disclosed in Studier and Moffatt, J. Mol. Biol. 1986 189: 113–130, incorporated herein by reference, may be used. In this system E. coli cells, transformed from plasmids containing the bacteriophage T7 promoter operatively linked with a nucleic acid sequence coding for a selected recombinant serine protease inhibitor, are infected with lambda phage having an expressible gene for T7 RNA polymerase. The cells are infected with phage after sufficient copies of the plasmid are present in the host cells and protein synthesis appears soon after infection.

Transformed host cells containing a nucleic acid sequence coding for a recombinant serine protease inhibitor can then be grown in an appropriate medium for the host. Where an inducible promoter is employed, the host cells are grown to high density and the promoter turned on for expression of the fusion protein and protease. Where the promoter is not inducible, then constitutive production of the protein product occurs. Constitutive production of these inhibitors is preferable only in expression systems where it is not substantially toxic to the host cell. The cells may be grown until there is no further increase in product formation or the ratio of nutrients consumed to product formation falls below the predetermined level, at which time the cells may be harvested, lysed and the protein product obtained and substantially purified in accordance with conventional techniques.

As used herein, host cells transformed with an appropriate expression vector, and cell cultures of such host cells can be used to synthesize recombinant serine protease inhibitors of the present invention. Protein preparations of the recombinant serine protease inhibitors can also be prepared from host cells and cell cultures.

Host cells are cultured in medium appropriate to maintain the cells and produce a mixture of cells and medium containing a recombinant serine protease inhibitor. Alternatively, the mixture may be purified. Purification methods which can be used include, but are not limited to, ion exchange chromatography, affinity chromatography, electrophoresis, dialysis and other methods of protein purification known in the art. Protein preparations comprising purified or unpurified recombinant serine protease inhibitors from the host cells are produced. These preparations comprise recombinant serine protease inhibitors and perhaps other materials from the mixture of cells and medium, depending upon the degree of purification of the protein.

Thus, the present invention provides a method of producing recombinant serine protease inhibitors such as the human α-1-antichymotrypsin analogues which comprises culturing a host cell capable of expressing a recombinant serine protease inhibitor and optionally purifying the mixture to produce a recombinant serine protease inhibitor in purified form.

The term "purified" when used to describe the state of nucleic acid sequences of the present invention refers to nucleic acid sequences substantially free of nucleic acids not coding for a recombinant serine protease inhibitor or other material normally associated with nucleic acids in nonrecombinant cells. The term "purified" or "in purified form" when used to described the state of a recombinant serine protease inhibitor protein, refers to a recombinant serine protease inhibitor free, to at least some degree, of cellular material. Preferably the recombinant serine protease inhibitor has a purity or homogeneity of at least about 25% to about 100%. More preferably the purity is about 50% or greater.

The serine protease inhibitors prepared in accordance with the teachings of the present invention can be used in the treatment of diseases related to the abnormal function of proteases or their inhibitors. For example, serine proteases such as elastase, cathepsin G, chymases and tryptases are associated with phagocytosis. Abnormal function of these proteases or their inhibitors is associated with inflammation, emphysema, adult respiratory distress syndrome (ARDS) and rheumatoid arthritis. Serine proteases such as trypsin, chymotrypsin, elastase and enterokinase are involved in digestion. The abnormal function of these proteases or their inhibitors is associated with pancreatitis. Serine proteases such as plasmin and plasminogen activator are associated with fibrinolysis. The abnormal function of these proteases or their inhibitors is associated with tumor invasion. Serine proteases such as Factor IXI, Factor Xa, Factor XIa, Factor XIIa, Factor VIIa, thrombin, activated protein C and plasma kallikrein are involved in blood coagulation. The abnormal function of any of these proteases or their inhibitors is associated with vascular clotting, cerebral infarction, and coronary infarction. Serine proteases such as Factor Clr, Factor Cls, Factor D, Factor B and C3 convertase are involved in complement activation. Abnormal function of these proteases or their inhibitors is associated with rheumatoid arthritis and inflammation. Serine proteases such as tissue kallikrein and post proline cleaving enzymes are involved in hormone generation and degradation. The abnormal function of these proteases or their inhibitors is associated with inflammation. Serine proteases such as plasmin, plasminogen activator and acrosin are involved in ovulation and fertilization. The function of these proteases and their inhibitors is associated with fertility control. ATP-dependent proteases are involved in protein turnover. Abnormalities associated with these proteases and their inhibitors are involved in muscle degradation and fever.

The recombinant serine protease inhibitors of the present invention are administered to a patient in an effective amount in the presence of a pharmaceutically acceptable carrier. By "effective amount" is meant a concentration of recombinant serine protease inhibitor which is capable of modulating an activity of a selected protease. This amount can be routinely determined by one of skill in the art in accordance with the weight, age and clinical condition of the patient. Suitable pharmaceutically acceptable carriers are well known in the art and are described, for example, in Gennaro, Alfonso, ed., *Remington's Pharmaceutical Sciences,* 18th edition, 1990, Mack Publishing Co., Easton, Pa., a standard reference text in this field. Suitable pharmaceutical carriers are selected in accordance with the intended route of administration and standard pharmaceutical practices. Such compositions can be administered by any suitable route including, but not limited to, intravenously, orally, intraperitoneally, intramuscularly, subcutaneously, topically, and by absorption through epithelial or mucocutaneous linings such as nasal, oral, vaginal, rectal, and gastrointestinal. The proportional ratio of active ingredient to pharmaceutical carrier will naturally depend on the chemical nature, solubility, and stability of the recombinant serine protease inhibitor. Compositions prepared in accordance with the disclosed invention may be administered either alone or in combination with other compounds, including but not limited to, other recombinant serine protease inhibitors, antibodies, toxins, and antisense oligonucleotides. These compositions are also useful in diagnosing and treating patients with deficient amounts of a wild type serine protease inhibitor. Familial α1-Antichymotrypsin (ACT) deficiency, defined as plasma levels of less than 64% normal, has been studied in patients and their relatives with partial deficiency of less than 50% normal. Six out of eight ACT deficient individuals, over 25 years of age, had liver abnormalities, while three out of eight ACT deficient individuals had lung abnormalities. These manifestations varied from severe disease to subtle laboratory abnormalities and appear to be related to an abnormal expression of ACT resulting from a deletion of one or two alleles in the gene for ACT which causes uncontrolled activity of the protease Chtr. Eriksson et al., *Acta Med Scand* 1986, 220, 447. Two defective mutants of human α1-antichymotrypsin (ACT) gene have also been associated with chronic obstructive pulmonary disease (COPD). Poller, W. et al., *Genomics*

1993, 17, 740. A leucine 55-to-proline substitution causing a defective ACT allele was observed in a family with COPD in three subsequent generations. Another mutation, proline 229-to-alanine, was associated with ACT serum deficiency in four patients with at positive family history. In each of these mutations, the physiological manifestations related to the mutation can be alleviated by early diagnosis and treatment of the deficiency. Identification of mutations using well known PCR or RT-PCR techniques and correlation with recombinant serine protease inhibitors of the present invention facilitates diagnosis of such conditions. In addition, the compositions of the invention are useful in treating these deficiencies.

The following nonlimiting examples are provided to further illustrate the present invention.

EXAMPLES

EXAMPLE 1: Construction and Purification of ACT Analogues

Beginning with the ACT expression vector, pACT, and using standard site-directed mutagenesis, a unique Kpn1 restriction site was created at position corresponding to P10–P9, changing Ala-Ala to Gly-Thr and a Mlu1 restriction site was created at P10'–P11', changing Val to Thr. The association rate constant of variant rACT encoded by this expression vector is $5 \times 10^6$ $M^{-1}S^{-1}$ and has an SI of 1 equivalent to wild type. Cassette variants were then created by removing the Kpn1-Mlu1 fragment and inserting a synthetic double strand oligonucleotide with selected coding sequences. The rACT-P10P10', rACT-P10P5" and rACT-OM mutants were generated in the cassette vector.

The point mutants rACT-T345R, rACT-A347R and rACT-A350R were generated by PCR using standard techniques. A pair of complementary internal primers which encoded a specific mutation were used separately by pairing with their respective external primers for two PCR reactions. The two PCR reactions gave two species which include the mutation site and have complementary ends. Two species mixed at equal molar concentration were used as a mutant template with two external primers for a PCR reaction to amplify the mutant gene. The point mutants rACT-T345R, rACT-A347R and rACT-A350R constructed in this manner were verified by nucleic acid sequencing.

Wild type rACT and mutants were purified by lysing the bacteria in a French press, followed by centrifugation and application of the supernatant to an anion exchange column which was eluted in a salt gradient. The active fraction was applied to a DNA cellulose column and eluted in salt. The pure product showed a single band on SDS-PAGE gel. Mutations prepared by this method are shown in Table 1.

TABLE 1

Mutations to Reactive Center Loop of Antichymotrypsin

| SEQ ID NO | Name | Sequence/Mutation P10   P5   P1P1'   P5'   P10' |
|---|---|---|
| 3 | rACT (wild type) | TEASAATAVKITLLSALVETRTIVRFN |
| 4 | rACT-L358M | :::::::::::::M::::::::::: |
| 5 | rACT-L358R | :::::::::::::R::::::::::: |
| 6 | rACT-L358W | :::::::::::::W::::::::::: |
| 7 | rACT-V-P3' | :::::::::::::::V::::::::: |
| 8 | rACT-P3P3' | :::::::::IPMSIP::::::::: |
| 9 | rACT-P6-P3 | ::::::::LEAIPMSIP::::::::: |
| 10 | rACT-CAS | :::::GT::::::::::::::T::: |

TABLE 1-continued

Mutations to Reactive Center Loop of Antichymotrypsin

| SEQ ID NO | Name | Sequence/Mutation P10   P5   P1P1'   P5'   P10' |
|---|---|---|
| 11 | rACT-CAS-F | :::::GT:::::::F:::::::::T::: |
| 12 | rACT-CAS-M | :::::GT:::::::::M:::::::::T::: |
| 13 | rACT-CAS-P3-P3' | :::::GT::::::IPMSIP:::::::T:::: |
| 14 | rACT-CAS-P3-P3'/L | :::::GT::::::IPLSIP:::::::T:::: |
| 15 | rACT-CAS-ElasW | :::::GT:::::VISAEWM:::::::T:::: |
| 16 | rACT-CAS-Try | :::::GTMFLEAIPMSIPPE:::::T::: |
| 17 | rACT-P10P5' | :::::GTMFLEAIPMSIPPE:::::A::: |
| 18 | rACT-P10P10' | :::::GTMFLEAIPMSIPPEVKFNT::: |
| 19 | rACT-T345R | R::::::::::::::::::::::::: |
| 20 | rACT-T347R | ::R::::::::::::::::::::::: |
| 21 | rACT-T350R | :::::R::::::::::::::::::: |
| 22 | rACT-PZM/P3P4'AP6'9' | :::::GTTAVKIIPMSIPPE////T::: |
| 23 | rACT-PI-P3'R | :::::::::::IPRSIP:::::::::: |
| 24 | rACT-Hep Cof II | :::::::::::MPLSTQ:::::::::: |
| 25 | rACT-Anti-Thrombin | :::::::::::AGRSLN:::::::::: |
| 26 | rACT-Ci Inhibitor | :::::::::::VARTLL:::::::::: |
| 27 | rACT-PAI | :::::::::::SARMAP:::::::::: |
| 28 | rACT-Anti-Plasmin | :::::::::::MSRMSL:::::::::: |
| 29 | rACT-Prot C. Inhi | :::::::::::TFRSAR:::::::::: |
| 30 | α1P1 (wild type) | TEAAGAMFLEAIPMSIPPEVKFNKPFT |

In this Table, the character ":" denotes the same amino acid as the wild type; and the character "/" denotes a deletion of the amino acid.

EXAMPLE 2: Inhibition of Human Neutrophil Elastase Activity

Human Neutrophil Elastase concentration was measured, assuming a specific activity of 0.0053 absorbency units (410 nm)/min/pmol/ml, with N-mMeO-Suc-Ala-Ala-Pro-Val-pNA, SEQ ID NO: 1, (final concentration 1.0 mM in 1% Me$_2$SBSO) in 100 mM Hepes, 500 mM NaCl, pH 7.5 at room temperature. The Chtr activity was measured, assuming a specific activity of 0.02 absorbency units (410 nm)/min/pmol/ml, with Suc-Ala-Ala-Pro-Phe-pNA, SEQ ID NO: 2, (final concentration 0.2 mM in 0.2% Me$_2$SO) in 500 mM Tris-HCl, 0.025% Tx-100, pH 8.3 at room temperature. Stoichiometry of inhibition (SI) analyses were carried out in 1 ml containing 100 mM Tris-HCl, pH 8.3, 0.005% (v/v) Triton X-100 and constant amount of Chtr (about 180 μM) and varying the concentration of rACT and mutants. The rate of inhibition by rACT mutants against Chtr were measured at 25° C. under second-order conditions in reaction mixture containing equimolar concentration of Chtr and mutants with inhibitory activity. Data from these experiments is shown in Table 2.

EXAMPLE 3: Inhibition of Cathepsin G activity

Cathepsin G from human neutrophils was obtained from Athens Research and Technology, Inc. (Athens, Ga.) and used without further purification-. The concentration of cathepsin G was determined under standard assay conditions (0.1M Hepes, 7.5 and 1 mM Suc-AAPF-p-NA at 37° C.) assuming a specific activity of 250 pmole of product per minute. Reactions of cathepsin G (250 nM) with rACT variants were performed at 25° C. in 0.1–0.2 ml of a solution containing one of the following buffers: PBS, pH 7.4; 0.1M Tris-HCl, pH 8.3; 1M Tris-HCl, pH 7.0; 1.0M NaPi, pH 7.0 or 1M NaPi, pH 8.3. After incubation with various amounts of inhibitor for 15 to 30 minutes, residual activities were measured spectrophotometrically by dilution (4–8 fold) of a sample aliquot in 0.8 ml standard assay buffer containing 4 mM substrate solution Suc-AAPF-pNA. Rates of substrate hydrolysis were constant over the 2 minute period used to determine residual activities, indicating the cathepsin G:ACT complexes were stable to dilution. Data from these experiments are shown in Table 2.

EXAMPLE 4: Inhibition of Chymotrypsin Activity

Chymotrypsin (Chtr) activity was measured, assuming a specific activity of 0.02 absorbency units (410 nm)/min/pmol/ml, with Suc-Ala-Ala-Pro-Phe-pNA, SEQ ID NO: 2, (final concentration 0.2 mM in 0.2% $Me_2SO$) in 500 mM Tris-HCl, 0.025% Tx-100, pH 8.3 at room temperature. Stoichiometry of inhibition (SI) analyses were carried out in a total volume of 1 ml containing 100 mM Tris-HCl, pH 8.3, 0.005% (v/v) Triton X-100 and constant amount of Chtr (about 180 $\mu$M) and varying the concentrations of rACT and mutants. The rate of inhibition by rACT mutants against Chtr were measured at 25° C. under second-order conditions in reaction mixture containing equimolar concentration of Chtr and mutants with inhibitory activity. Data from these experiments are shown in Table 2.

EXAMPLE 5: Inhibition of Chymase Activity

Chymase was purified and its concentration determined as described by Schecter et al., *J. Biol. Chem.* 1993, 268, 23626. Inhibition of chymase by various rACT inhibitors was determined by titration. Chymase (200 nM) was titrated with increasing amounts of rACT variants in reactions containing 1 to 2M NaCl/0.1M Tris-HCL containing 0.01% Triton X-100, pH 8.0, at 25° C. This was accomplished using several reactions of 50 to 100 $\mu$l total volume containing an identical amount of chymase and varied amounts of rACT variants. Residual activities after suitable incubation periods were determined by removing an aliquot from each reaction, diluting it to 1 ml with assay buffer containing 1 mM Suc-Ala-Ala-Pro-Phe-pNA (SEQ ID NO: 2) substrate, and monitoring pNA release spectrophotometrically at 410 nm for 3 minutes. Rates of substrate hydrolysis were constant over the 3 minute monitoring period indicating that chymase-ACT complexes were stable to dilution and that residual activities obtained with this method were a reliable measurement of free enzyme in titration reactions. Data was converted to fractional activity and plotted against the $[I]_0/[E]_0$ ratio of each reaction to determine the stoichiometry of inhibition. The rate constant ($k_{obs}/I$) of chymase inhibition by various rACT inhibitors was measured under pseudo-first order conditions in the presence of substrate. Inhibitor concentrations were at least 10 fold higher than the enzyme concentration multiplied by the SI. Observed inhibition rate constants calculated from the data were corrected for the presence of substrate to obtain $k_{obs}/I$ values. Data from these experiments are shown in Table 2.

TABLE 2

Effect of Mutation to Reactive Loop of Antichymotrypsin on Enzyme Inhibition

| SEQ ID NO | Chymotrypsin Inhibition | Cathepsin-G Inhibition | Chymase Inhibition | Human Neutrophil Elastase Inhibition | Thrombin Inhibition | Plasmin Inhibition |
|---|---|---|---|---|---|---|
| 3 | a | a | p | i | p | |
| 4 | a | a | p | p | | |
| 5 | p | p | i | | a | a |
| 6 | | | v | | | |
| 7 | a | | a | | | |
| 8 | a | a | a | a | | |
| 9 | a | | | p | | |
| 10 | a | a | p | i | p | i |
| 11 | v | v | p | | | |
| 12 | a | a | p | p | | |
| 13 | a | a | a | a | | |
| 14 | a | | | i | | |
| 15 | i | | | i | | |
| 16 | i | | | | | |
| 17 | p | | | i | | |
| 18 | p | | | i | | |
| 19 | i | i | | i | | |
| 22 | a | | | a | | |
| 30 | | | | a | | |

In Table 2:
"v" means very active, better that any natural serpin inhibitor;
"a" means active;
"p" means partially active; and
"i" means inactive.

What is claimed is:

1. A method of diagnosing patients suspected of having a mutation in a gene encoding a serine protease inhibitor which results in uncontrolled activity of a protease comprising:
    (a) obtaining a biological sample from a patient suspected of having a condition characterized by uncontrolled activity of a protease;
    (b) identifying the serum protease inhibitor which is associated with the condition;
    (c) detecting mutations in the gene encoding said serine protease inhibitor; and
    (d) correlating the identified serine protease inhibitor with a recombinant serine protease inhibitor which controls activity of the protease wherein said recombinant serine protease inhibitor contains a protease binding site and a hinge region of a reactive loop which have modified amino acid sequences.

2. The method of claim 1 wherein the mutation is detected by PCR or RT-PCR.

3. The method of claim 1 wherein the condition comprises inflammation, fertility control, tumor migration, neurotropism, heat shock, acute myocardial infarctions, burns, autoimmune diseases, malignancies, infections or liver allograft rejection.

4. The method of claim 1 wherein the recombinant serine protease inhibitor comprises an analogue of human wild type α-1-antichymotrypsin wherein the amino acid corresponding to alanine at amino acid position 350 of wild type α-1-antichymotrypsin is substituted with arginine.

5. The method of claim 1 wherein the recombinant serine protease inhibitor comprises an analogue of human wild type α-1-antichymotrypsin wherein amino acids corresponding to Ala-Ala-Thr-Ala-Val-Lys-Ile-Thr-Leu-Leu-Ser-Ala-Leu-Val-Glu-Thr-Arg-Thr-Ile-Val at amino acid positions 349 to 368 of wild type α-1-antichymotrypsin are substituted with Gly-Thr-Met-Phe-Leu-Glu-Ala-Ile-Pro-Met-Ser-Ile-Pro-Pro-Glu-Val-Lys-Phe-Asn-Thr.

6. The method claim 1 wherein the recombinant serine protease inhibitor comprises an analogue of human wild type α-1-antichymotrypsin wherein amino acids corresponding to Ala-Ala-Thr-Ala-Val-Lys-Ile-Thr-Leu-Leu-Ser-Ala-Leu-Val-Glu at amino acid positions 349 to 363 of wild type α-1-antichymotrypsin are substituted with Gly-Thr-Met-Phe-Leu-Glu-Ala-Ile-Pro-Met-Ser-Ile-Pro-Pro-Glu and amino acid Val at position 368 is substituted with Ala.

* * * * *